United States Patent [19]

Herrick

[11] Patent Number: 5,723,005
[45] Date of Patent: Mar. 3, 1998

[54] PUNCTUM PLUG HAVING A COLLAPSIBLE FLARED SECTION AND METHOD

[75] Inventor: Robert S. Herrick, Rialto, Calif.

[73] Assignee: Herrick Family Limited Partnership, Rancho Cucamonga, Calif.

[21] Appl. No.: 475,548

[22] Filed: Jun. 7, 1995

[51] Int. Cl.$^6$ ..................................... A61F 2/14
[52] U.S. Cl. ..................................... 623/4; 604/8
[58] Field of Search .................. 128/887; 604/294, 604/8, 285; 623/4

[56] References Cited

U.S. PATENT DOCUMENTS

| | | | |
|---|---|---|---|
| 3,949,750 | 4/1976 | Freeman . | |
| 4,461,295 | 7/1984 | Herrick . | |
| 4,660,546 | 4/1987 | Herrick . | |
| 4,915,684 | 4/1990 | MacKeen et al. | 604/8 |
| 4,959,048 | 9/1990 | Seder et al. | 604/9 |
| 5,049,142 | 9/1991 | Herrick et al. | 604/294 |
| 5,053,030 | 10/1991 | Herrick et al. | 604/890.1 |
| 5,163,959 | 11/1992 | Herrick | 623/11 |
| 5,171,270 | 12/1992 | Herrick | 623/11 |
| 5,283,063 | 2/1994 | Freeman | 424/427 |
| 5,318,513 | 6/1994 | Leib et al. | 604/8 |
| 5,417,651 | 5/1995 | Guena et al. | 604/8 |
| 5,423,777 | 6/1995 | Tajiri et al. | 604/294 |

OTHER PUBLICATIONS

Article entitled *The Punctum Plug: Evaluation of a New Treatment for the Dry Eye*, by Jerre M. Freeman, MD, which appeared at pp. OP–873 through OP–879 in the American Academy of Ophthalmology and Optometry, vol. 79, Nov.–Dec., 1975 (the "Freeman Reference").

Article entitled *Intra–Canaliculer Gelatin Implants In The Treatment Of Kerato–Conjunctivitis Sicca*, by Wallace S. Foulds, which appeared at pp. 625–627 in the Brit. J. Ophthal., vol. 45, 1961 (the "Foulds Reference").

Article entitled *Punctal Occlusion With N–Butyl Cyaoacrylate Tissue Adhesive*, by James T. Patten, MD, which appeared at pp. 24–26 in Ophthalmic Surgery, vol. 7, No. 2, Summer 1976 (the "Patten Reference").

Product Brochure for a punctum plug referred to as the Umbrella Plug S2–3802, by J. A. Bernard, MD (the "Umbrella Plug Brochure"); and.

Product Brochure for a tapered shaft punctum plug referred to as the Super Plug, sold by Eagle Vision (the "Tapered Shaft Punctum Plug Brochure").

(List continued on next page.)

*Primary Examiner*—David H. Willse
*Attorney, Agent, or Firm*—Daniel J. Meaney, Jr.

[57] ABSTRACT

A punctum plug adapted to be inserted into the punctum opening of an eye and which is adapted to be transported into the vertical portion of the canaliculus or into the ampula to occlude the punctum opening and vertical portion of the canaliculus is shown. The punctum plug, or implant, comprises an elongated member having a pair of ends wherein one of the pair of ends includes a collapsible flared section which has a sloped or curved outer surface and the other end of the pair of ends includes a thin retaining lip to engage the edge of the punctum opening. The elongated member and collapsible flared section are formed of a dimension to pass through the punctum opening of an eye. The collapsible flared section has an extended position and a collapsed position. A radial force is applied against the outer surface of the collapsible flared and in a direction to collapse the collapsible flared section which urges the same from its extended position into the collapsed position. As the collapsible flared section passes through the punctum opening and vertical section of the canaliculus, a clamping force is developed. When the collapsible flared section passes into the ampula, it reverts back to its substantially extended position in the ampula to occlude the punctum and vertical portion of the canaliculus. A method for treating external eye condition due to a deficiency of tears utilizing the punctum plug is also shown.

44 Claims, 6 Drawing Sheets

OTHER PUBLICATIONS

Article entitled *Diagnosis and Treatment of Keratoconjunctivitis Sicca*, by Jose I. Barraquerm MD, et all, which appeared at p. 43 in the Symposium on Medical and Surgical Diseases of the Cornea, Transactions of the New Orleans Academy of Ophthalmology, C. V. MoshbyCo. publisher, 1980 (the "Barraquer Reference").

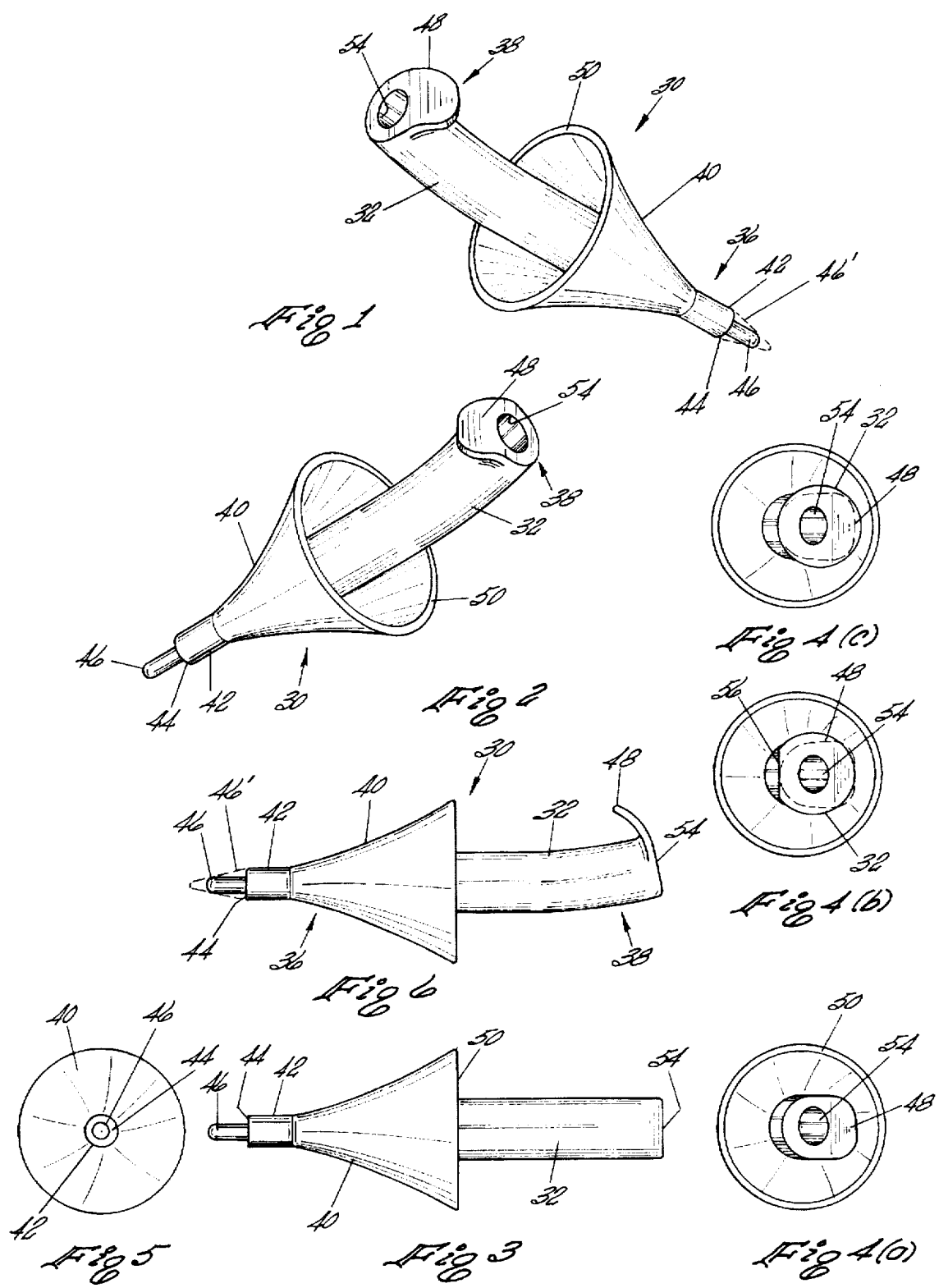

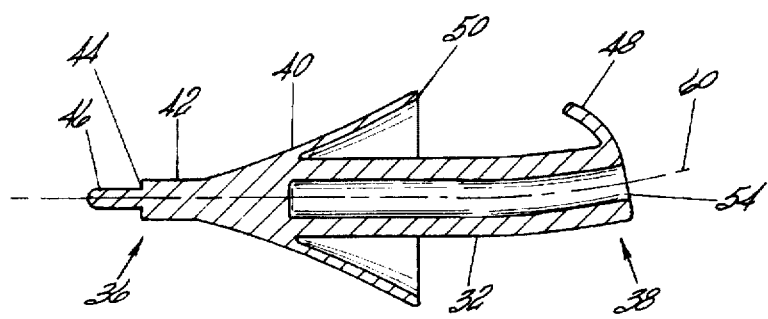
Fig 7
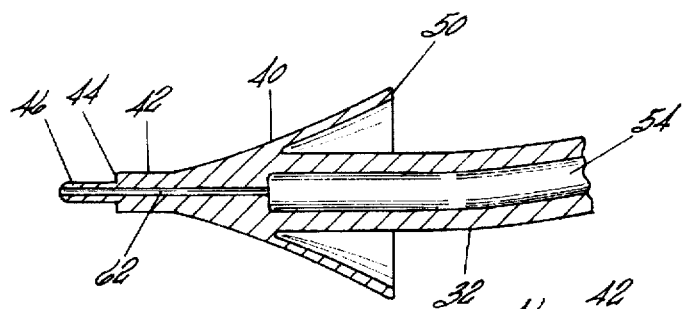
Fig 8
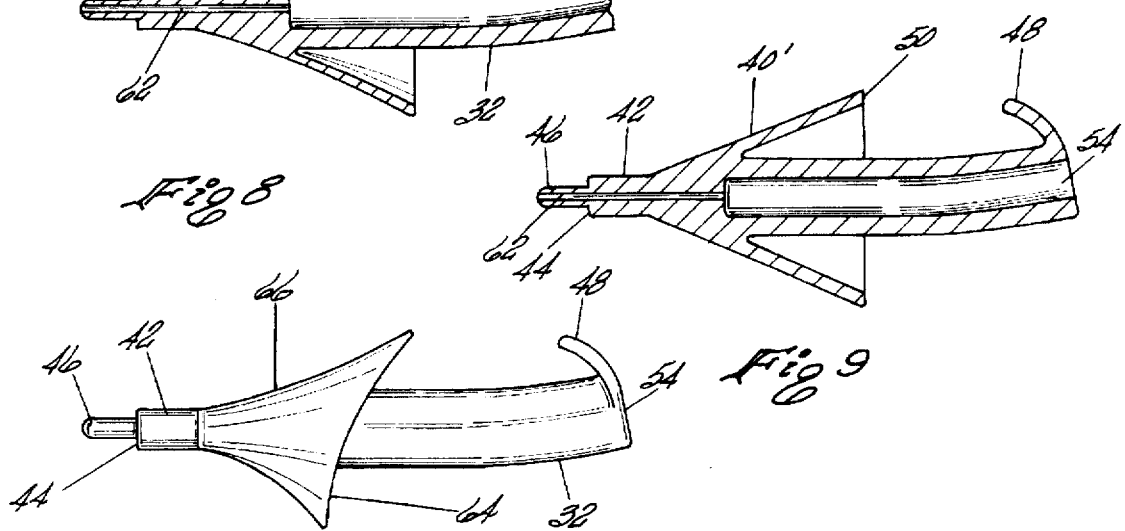
Fig 9
Fig 10
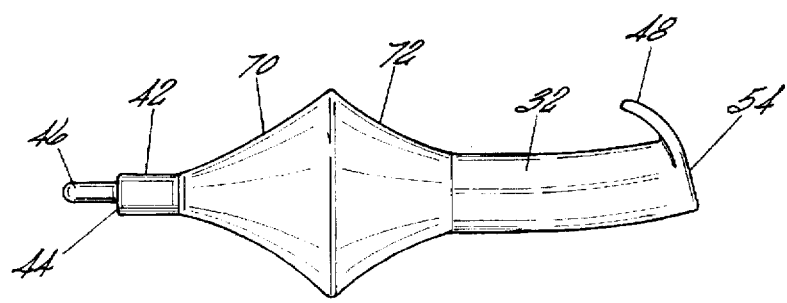
Fig 11

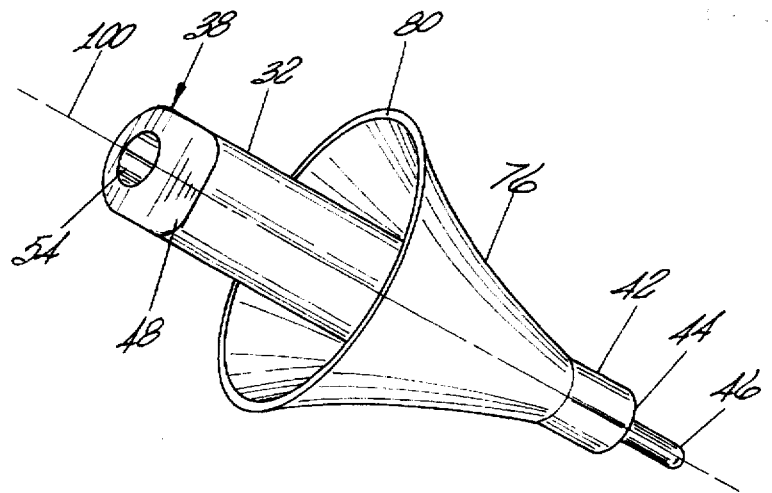
Fig 12
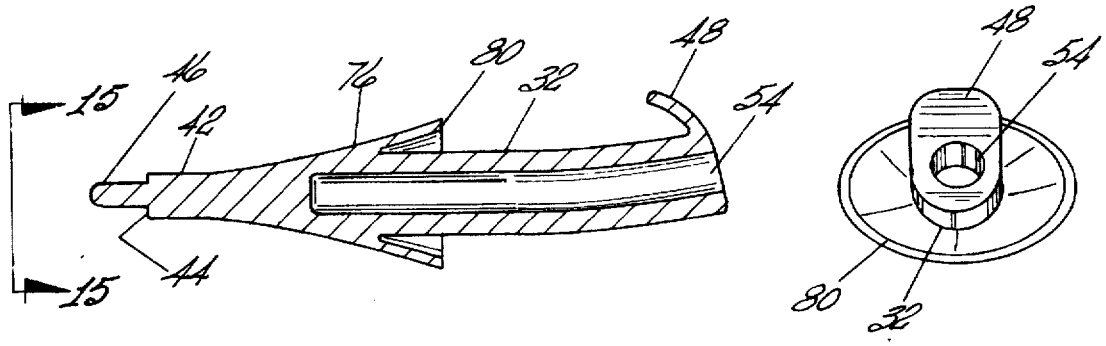
Fig 13
Fig 14
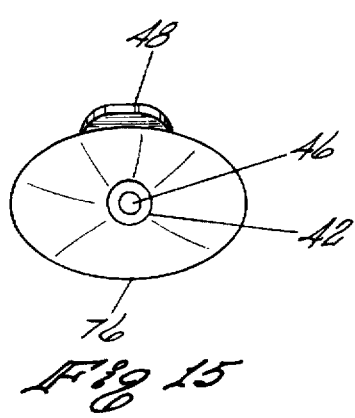
Fig 15

PUNCTUM PLUG HAVING A COLLAPSIBLE FLARED SECTION AND METHOD

BACKGROUND OF THE INVENTION

1. Field of the Invention

This invention relates to a punctum plug adapted to be utilized in the treatment of a human eye having a deficiency of tears and more specifically relates to a punctum plug or implant having an elongated member having means defining a collapsed flared section at one end thereof and a thin elongated retaining tip at the other end thereof. The elongated member and the collapsible flared section are dimensional to pass through the punctum of an eye.

This invention also relates to a method for treating external eye conditions due to a deficiency of tears utilizing the punctum plug or implant having a collapsible flared section at one end thereof.

2. Description of the Prior Art

It is known in the art that certain eye problems are related to the volume of tears on the surface of the eyes. Certain of these problems include dry eyes, corneal ulcer, conjunctivitis, blepharitis, contact lens problems and many other external eye diseases.

One method for treating for a deficiency of tears is disclosed in U.S. Pat. No. 4,660,546, wherein the inventor is the same inventor of the present invention. U.S. Pat. No. 4,660,546 discloses a method for treating external human eye conditions due to a deficiency of tears which includes the step of temporarily blockading the canaliculus of the patient and observing over a preselected period of time the response of the patient's eye to the temporary blockage and to determine if any improvement in the eye condition has been achieved in response to the occlusion. If an improvement in eye condition is noted, an implant is placed within the horizontal portion of at least one of the canaliculi of the patient. A temporary blockading of the canaliculus is performed by placing a dissolvable, removable element, which may be in the form of a collagen material or other dissolvable material such as, for example, catgut, in the canaliculus. Unless removed shortly after insertion, the dissolvable implant is absorbed by the body in approximately a two week period. A determination is first made if the canaliculus blockage results in an improvement in the eye condition or other conditions caused by related nasal congestion warranting permanent blockage of the canaliculus, for example, the patient will respond to a partial 60% to 80% retention of constant tears. If permanent blockage of the canaliculus is warranted, U.S. Pat. No. 4,660,546 discloses that the permanent blocking of the canaliculus is performed by utilizing a permanent implant. U.S. Pat. No. 4,660,546 discloses that the permanent implant is fabricated of a nonabsorbable or non-dissolvable material and is in the form of a cylindrically shaped central body having a tapered end or an end of reduced diameter to facilitate the implantation of the implant into and for removal of the implant from the canaliculus. Both the temporary collagen implant or other dissolvable material and the permanent implant disclosed in U.S. Pat. No. 4,660,546 are in the form of a cylindrically shaped central member having a predetermined diameter which may terminate at one end in a tapered end and which reduces in diameter as it slopes away from the central member to form a tapered tip to facilitate insertion of the implant through the punctum, through vertical canaliculus and into the horizontal portion of the canaliculus.

U.S. Pat. No. 4,461,295, wherein the inventor thereof is the same as the inventor of the present invention, discloses another treatment method which is a method for laser punctal occlusion. It is known in the art that punctal occlusion has been proven to be an effective way of treating patients with conditions such as sinusitis, hay fever, middle eye infection (chronic), post nasal drip, front headache and other such conditions. The treatment method disclosed by U.S. Pat. No. 4,461,295 includes the use of a temporary suture to stitch the tear drainage canals of the eyes closed to determine if a greater tear volume on the surface of the eyes would improve certain eye problems. This diagnostic procedure has become known in the art as the Herrick Stitch Test. The Herrick Stitch Test is performed by anesthetizing the local area around the lower or upper punctum of the eye. A stitch is carefully placed to occlude the punctum by an eye surgeon utilizing magnification of the eye. After a preselected period of time using the Herrick Stitch Test, the eye surgeon determines if the eye condition has improved, if so, then the eye surgeon permanently closes the punctum by using an ARGON laser. The punctum may be reopened at a later time if excess tearing is experienced. The reopening of the punctum can be performed by surgical and laser techniques, all as disclosed in U.S. Pat. No. 4,461,295.

It is also known in the art to utilize other plugs and or techniques for occluding the punctum. One plug device which is known in the art is referred to as a punctum plug which is described in an article by Jerre M. Freeman, MD, entitled "The Punctum Plug: Evaluation of a New Treatment for the Dry Eye" which appeared in the publication of the transcripts of the America Academy of Ophthalmology and Optometry, pages OP-874 through OP-879 (hereinafter referred to as the "Freeman Reference"). In addition, the same punctum plug is disclosed and described in U.S. Pat. No. 3,949,750.

The punctum plug disclosed in the Freeman Reference and in U.S. Pat. No. 3,949,750 is a plug which is adapted to be inserted into the upper and/or lower punctal openings of the eye to block or occlude the punctum. The punctum plug of Freeman is a rod-like plug formed with an oversized rigid or solid tip or barb portion that dilates and blockingly projects into the vertical portion of the canaliculus. The punctum plug has a smaller neck or waist portion around which the punctum sphincter ring tightens. The punctum plug has relatively large, smooth head portion which rests on top of the punctal opening and prevents the plug from passing down into the canaliculus. The smooth head portion is designed to be domed shaped to permit the head to rest in the lacrimal lake and against the conjunctiva and cornea with little irritation. The head portion functions to prevent the punctum plug from passing into the horizontal portion of the canaliculus. The punctum plug of Freeman is subject to being inadvertently removed from the eye by the patient.

It is also known in the art to provide for a temporary closure of the punctum by heat using a light cautery around and in the punctal opening. The punctal closure procedure is disclosed in an article entitled "Diagnosis and Treatment of Keratoconjunctivitis Sicca" which appeared in a symposium on medical and surgical diseases of the cornea, transactions of the New Orleans Academy of Ophthalmology in 1980 at page 43 wherein the authors thereof were Jose I. Barraquer, MD and eight other authors (hereinafter referred to as the "Barraquer Reference"). The Barraquer Reference further discloses that other treatment methods of temporarily closing the punctum include use of gelatin plugs, cyanoacrylate adhesives and diathermy. The use of intracanalicular gelatin implants for treatment of eye conditions is described in an article entitled "INTRA-CANALICULER GELATIN IMPLANTS IN THE TREATMENT OF KERATO- CONJUNCTIVITIS SICCA" by Wallace S. Foulds which appeared in the Brit J. Ophthal (1961) in Volume 45 at pages 625 through 627, inclusive, (the "Foulds Reference"). The Foulds Reference discloses that occlusion of the lacrimal puncta can be performed by use of and insertion of a fine, water soluble gelatin rod into the punctal openings. The gelatin rod is formed from pure powdered gelatin to which a small quantity of distilled water has been added and is heated in a water bath until the gelatin dissolves and a thick gel results. By dipping a cold glass rod into the so prepared gelatin, and withdrawing the same, fine solid rods of gelatin were formed. The so formed gelatin rods were then inserted into the canaliculi to provide a temporary blockage. As such, the gelatin rod implants, although very fragile, provide an alternate known means for temporarily blocking the canaliculus. If an improvement in eye condition is obtained, then permanent closure of the canaliculi may be warranted.

It is known in the art that a Schirmer's test can be utilized to measure gross tear secretion. If the results of the Schirmer tear secretion test discloses that an insufficient portion of the tear secretion is retained on the eyes, a temporary or permanent occlusion of the canaliculi may prove helpful to improving the above described external eye conditions.

An improvement over the Freeman punctum plus described in U.S. Pat. No. 3,949,750 is shown in U.S. Pat. No. 4,915,684. U.S. Pat. No. 4,915,684 discloses a lacrimal fluid modulating device composed of a generally cylindrical body portion with an enlarged cap at one inlet and a tapered peripheral enlargement at an outlet end. The tapered peripheral enlargement is solid. An axial bore extends completely through the modulating device and is fashioned with an outlet end having an internal diameter which is preferably no less than 0.12 and no greater than 0.36 mm.

A tapered shaft punctum plug for occlusion of the punctum opening having a tapered shaft and including one end that terminates in a narrow neck and a concave dome and another end that terminates in a solid pointed nose is offered for sale by Eagle Vision under the trademark SUPER PLUG.

Another punctum plug that is commercially available for occluding the punctum opening is known as an UMBRELLA PLUG. The UMBRELLA PLUG has an elongated cylindrically shaped central member having one end that is cut at an angle relative to the central axis and terminates in a flat, circular washer like cap or collarette. The UMBRELLA PLUG has at its other end a collapsible umbrella shaped bulb which collapses like the closing of an umbrella during insertion of the umbrella shaped bulb through the punctum and when the umbrella has passed through the punctum opening, it then reverts back to an open position.

As is evidenced by the above described prior art, the two approaches used to occlude the lacrimal drainage system are to: (a) occlude the punctum opening and vertical portion of the canaliculus, e.g., Freeman U.S. Pat. No. 3,949,750, U.S. Pat. No. 4,915,684 the SUPER PUNCTUM PLUG and the UMBRELLA PLUG; and (b) occlude the horizontal portion of the canaliculus, e.g., U.S. Pat. Nos. 4,660,546 and 5,049,142. However, other implants which can be used to occlude either the vertical portion or the horizontal portion of the canaliculus are U.S. Pat. Nos. 5,163,959 and 5,171,270 wherein the inventor thereof is the same inventor as in the present Application.

In practice, however, it has developed that the transition from the vertical portion of this canaliculus to the horizontal portion of the canaliculus does not occur as a distinct transition point, but rather occurs through an intermediary section referred to as the ampula or sac.

Therefore, an implant which occludes the punctum opening and vertical section of the canaliculus, depending on its length, can have a portion thereof located in the ampula or sac. By occluding the lacrimal drainage system in this manner, it is not necessary that the implant physically be located in the horizontal portion of the canaliculus to be effective. On the other hand, if an implant, without a dome or collarette, is inserted into the punctum opening or the vertical section of the canaliculus, that implant generally migrates through the punctum opening through the vertical section of the canaliculus, into the ampula or sac, and can easily migrate into the horizontal portion of the canaliculus.

SUMMARY OF THE PRESENT INVENTION

The present invention discloses a new, novel and unique punctum plug or implant which comprises an elongated central member having a medial end which terminates in a thin retaining lip which can be positioned over the edge of the punctum opening of the eye and away from the cornea. The punctum plug includes a medial end having a collapsible flared section. In the preferred embodiment of the present invention, the punctum plug or implant is adapted to be inserted into the punctum opening of an eye and to be transported into the vertical portion of the canaliculus, and if of sufficient length, into the ampula of the canaliculus to occlude the punctum opening and vertical portion of the canaliculus. The punctum plug includes an elongated member having a medial end and a spaced, opposed lateral end and a central member. In the preferred embodiment, the medial end is slightly angularly disposed from the lateral end. The lateral end has a collapsible flared section which terminates in an outer edge having dimension which is greater than the cross-sectional dimension of the central member. The collapsible flared section has an expanded position and a collapsed position wherein the dimension of the collapsed position is approximately equal to the geometrical dimension of the punctum opening of an eye adapted to receive the same. The application of a radial force to the collapsible flared section in a direction to collapse the outer edge thereof urges the collapsible flared section from its extended position into its collapsed position. If the length of the punctum plug is selected to keep the collapsible flared section within the vertical portion of the canaliculus, the clamping force developed between the collapsible flared section and interior side walls of the vertical portion of the canaliculus holds the punctum plug in place.

If the punctum plug has sufficient length, once the collapsible flared section passes through the punctum opening and vertical portion of the canaliculus into the ampula or sac, it reverts back to its substantially extended position. The canalicular implant may be fabricated from a biodegradable material if it is to be used as a temporary implant, or may be formed of a non-biodegradable material if it is to be used as a permanent implant.

The known prior art implants for providing temporary and permanent occlusion of the punctum opening and vertical portion of the canaliculus has certain disadvantages. One disadvantage is that a temporary implant, disclosed by the prior art, may have to be removed before it has been fully dissolved or absorbed, as the case may be. If the eye surgeon is unable to remove any part of or all of the temporary implant, the portion of the temporary implant not removed must remain in the canaliculus until it ultimately is dissolved in the body thereby terminating the occlusion of the canaliculus. Typically, an eye surgeon will utilize the temporary implant as a means for determining if the permanent occlusion of the canaliculi will result in an improvement of eye conditions as described hereinbefore. It is possible for the temporary collagen implant if inserted into the punctum opening or vertical portion of the canaliculus, for example, to migrate into the horizontal portion of the canaliculus or back out of the eye or to otherwise not remain in place. Also, the temporary implants may be too fragile to remove in a single piece during removal thereof, if required, by the eye surgeon.

In addition, the insertion and use of a permanent implant having a central body and a tapered end, which is usually formed of a nonabsorbable or non-dissolvable material, can be utilized to permanently occlude either the vertical portion or the horizontal portion of the canaliculus. However, such a permanent implant can still migrate within the lacrimal system and into the horizontal portion of the canaliculus or out of the eye. Any migration of a permanent implant is undesirable.

The laser treatment to obtain punctal occlusion, although quite effective, has certain disadvantages. One disadvantage is injection of a local anesthetic is required and the patient may experience some pain or discomfort for one to two days after the procedure. Also, some discharge may occur for seven to ten days. Vision may be blurred for a few days. If the patient wears contact lens, the contact lens may be uncomfortable for a few days.

The other known punctum plugs have a convex dome or collarette to act as a cap to prevent the punctum plug from migrating through the punctum opening, through the vertical portion of the canaliculus, into the ampula or sac or into the medial position of the horizontal portion of the canaliculus. Such caps are generally circular and result in an edge which engages, contacts or otherwise abrades the cornea.

Therefore, one advantage of the canalicular implant of the present invention is that the punctum plug or implant, when positioned in the punctum opening of the canaliculus, will be held in place and restricted from movement by a thin elongated lip which is urged against the edge or sphincter muscle of the punctum opening and the collapsible flared section of the implant located within the vertical portion of the canaliculus or within the ampula.

Another advantage of the present invention is that the implant includes a collapsible flared section which has an outer edge which is slideably urged against the interior walls of the punctum opening during insertion and placement within the vertical portion of the canaliculus to hold the implant in position while concurrently occluding the canaliculus.

Another advantage of the present invention is that the canalicular implant is relatively easy to insert without the necessity of using an injectable anesthetic.

Another advantage of the present invention is that the permanent implant, when positioned in the punctum opening and vertical portion of the canaliculus, does not cause any tissue irritation or irritation to the eye due to migration of the same out of the canaliculus and through the punctum opening into the eye.

Another advantage of the present invention is that the punctum plug or implant is easily removable and does not cause any discomfort, does not cause any pain to the patient or to the cornea of the eye of a patient, there is no discharge for several days, the patient's vision is not subject to blurring for several days and, if the patient wears contact lens, the contact lens will not be uncomfortable for several days.

Another advantage of the present invention is that due to the holding action between the collapsible flared section of the medial end of the implant and the thin retaining lip of the lateral end which is urged against the sphincter muscle of the punctum opening, the canalicular implant cannot be easily or readily dislodged by patient activity or movement.

Another advantage of the present invention is that the punctum plug or implant causes no long term discomfort to the user when the same is in place.

Another advantage of the present invention is that the punctum plug or implant is effective in blocking a drainage of tears through the punctum opening and the vertical portion of the canaliculi. Thus, if only a partial blockage of drainage of tears is required, the punctum plug or implant can having a fluid metering opening extending axially therethrough.

Another advantage of the present invention is the collapsible flared section of the punctum plug or implant can include a hollowed out central area which defines a thin walled, conical-shaped flared section.

Another advantage of the present invention is that the thin walled, conical-shaped flared section can terminate in an outer edge.

Another advantage of the present invention is that the elongated member may have a slight angular curve to urge the thin retaining lip into engagement with the edge of the punctum opening and away from the cornea.

Another advantage of the present invention is that the collapsible flared section can be non-uniform such as being cut at a bias or having a non-circular cross-section, such as being elliptically shaped.

Another advantage of the present invention is that the collapsible flared section of the canalicular implant can include a tool receiving opening in the central section thereof which is adapted to cooperate with an insertion tool.

Another advantage of the present invention is that the cross-section diameter of the central member preferably would have a diameter of about 0.3 mm to about 1.2 mm while the outer edge of the collapsible flared section can have a diameter in the order of about 0.5 mm to about 2.2 mm.

Another advantage of the present invention is that the punctum plug or implant can be formed of a nonabsorbable or non-dissolvable material such as silicone, polytetrafluoroethylene (e.g. Teflon) or other medically compatible non-biodegradable material.

Another advantage of the present invention is that the punctum plug or implant could be formed of an absorbable or dissolvable material to function as a temporary implant. One such absorbable or dissolvable material that could be utilized for practicing this invention is collagen.

Another advantage of the present invention is that the length of the punctum plug can be selected to place the collapsible flared section in the vertical portion of the canaliculus or place the collapsible flared section in the ampula.

Another advantage of the present invention is that a method for treating an external eye condition due to a deficiency of tears using the punctum plug of the present invention which can be used for treating an eye.

BRIEF DESCRIPTION OF THE DRAWINGS

The foregoing and other advantages of this invention will be apparent from the following description of the preferred embodiment of the invention when considered with the illustrations and accompanying drawings which include the following Figures:

FIG. 1 is a front, top and right end perspective view of a punctum plug of the preferred embodiment having a thin elongated retaining lip at the lateral end and a collapsible flared section at the medial end;

FIG. 2 is a bottom, rear and right end perspective view of the punctum plug of FIG. 1;

FIG. 3 is a front elevational view thereof;

FIGS. 4(a), 4(b) and 4(c) are a right side elevational view of FIG. 3; an alternate structure having a chamfered edge and an eccentric variation, respectively, to prevent the lateral end from contacting the cornea;

FIG. 5 is a left side elevational view thereof;

FIG. 6 is a bottom elevational view thereof;

FIG. 7 is a cross-sectional view of the punctum plug of FIG. 1, having tool receiving opening in the center of the collapsible flared section having uniformly sloping side walls which is adapted to cooperate with an insertion tool;

FIG. 8 is a cross-sectional view of an alternate embodiment of FIG. 7 having a fluid metering opening extending therethrough; punctum plug tool receiving opening within a collapsible flared section having curved sloping walls which is adapted to cooperate with an insertion tool;

FIG. 9 is a cross-sectional view of yet another embodiment of a punctum plug having an elongated tool receiving opening which is adapted to cooperate with an insertion tool and wherein a fluid metering opening extends through and out the medial end;

FIG. 10 is a bottom elevational view of yet another embodiment of the punctum plug wherein the collapsible flared section has curved outer walls and wherein the outer edge is cut on the bias relative to the central axis of the elongated member;

FIG. 11 is a bottom elevational view of yet another embodiment of the punctum plug wherein the collapsible flared section is formed by two conical-shaped members having curved outer walls wherein the outer edges thereof are joined to form a bellows shaped collapsible flared section;

FIG. 12 is a modification of the embodiment of FIG. 6 wherein the elongated member has a relatively straight central axis;

FIG. 13 is a cross-sectional bottom elevational view of yet another embodiment of a punctum plug having a collapsible flared section which is elliptically shaped;

FIG. 14 is a right end elevational view of FIG. 13;

FIG. 15 is a left end elevational view of FIG. 13;

FIGS. 22(a) through 22(c) are pictorial representations of the steps of insertion of a punctum plug of the present invention into the punctum opening and canaliculus wherein FIG. 22(a) illustrates the punctum plug being passed through the punctal opening; FIG. 22(b) illustrates the punctum plug passing through the vertical portion of the canaliculus; and FIG. 22(c) illustrates the collapsible being positioned within the ampula or sac.

DESCRIPTION OF THE PREFERRED EMBODIMENT

Figure 16:
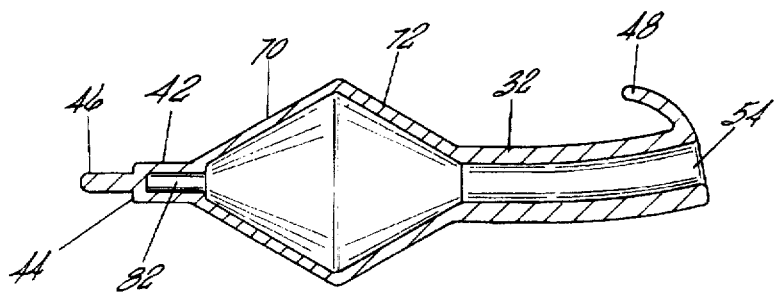
FIG. 16 is a cross-sectional bottom elevational view of yet another embodiment of a collapsible flared section in the form of a bellows defined by two conical-shaped collapsible flared sections having sloped outer walls and joined at the outer edges or outer rings.

The following description of Figs. applies generally to FIGS. 1 through 6 and uses the same reference numerals for reference to the same elements. Similar reference numerals are used in the other Figs.

As illustrated in FIGS. 1 through 6, the implant, which in the preferred embodiment is a punctum plug, is shown generally as 30 and includes an elongated member 32 having a pair of ends 36 and 38. One of the pair of ends, in the preferred embodiment the medial end, 36 includes a collapsible flared section 40 having an outer surface. The other of said pair of ends, in the preferred embodiment the lateral end, 38 includes a thin retaining lip. The elongated member 32 and the collapsible flared section 40 is formed of a dimension to pass through a punctum opening and vertical portion of the canaliculus of an eye.

For purposes hereof, the term "thin elongated lip" means a thin elongated lip which is located on the elongated member to position the thin elongated tip in a generally anterior direction upon insertion in to a punctum opening and which extends or protrudes beyond the outer surface of the elongated member and which would be located around approximately 300° or less of the periphery of the elongated member to engage the eyelid leaving the posterior surface thereof free from protruding into, or from contacting with or from abrading the cornea or conjunctiva of an eye. This can be accomplished in any way including the embodiments disclosed herein such as FIGS. 1, 4(a), 4(b) and 4(c) which are exemplary.

In the preferred embodiment, the elongated member 32 curves slightly in a direction towards the other of said pair of ends 38. Thus, the end 38 is slightly angularly disposed relative to the one end 36. The end 36 includes a tip insert section 42 having a shoulder 44 and a distal starting tip 46 which is smaller in cross-sectional dimension than the tip insert section 42. In the alternative, the distal starting tip 46 may be a tapered end shown as 46'.

The collapsible flared section 40, is illustrated to have curved outer wall and defines a thin walled, conical shaped member which terminates in the outer edge or outer ring 50. In the embodiment in FIG. 1, the cross-section of the conical shaped collapsible flared section 40 is generally circular. The collapsible flared section 40 is located between the pair of ends 36 and 38 and is located adjacent to the medial end 36.

The other end 38, or the lateral end, terminates in a thin retaining lip 48 which is located at a selected position on end 38. The thin elongated end 48 is operatively connected to the lateral end 38 so as to be positioned away from the cornea when the implant has been inserted into the eye. An elongated opening 54 extends from the lateral end 38 to a location intermediate the conical-shaped collapsible flared section 40 and this is shown in greater detail in FIG. 7.

FIG. 4(a) illustrates one structure where the thickness of the lateral end 38 is controlled or selected to avoid contact with the cornea. FIGS. 4(b) and 4(c) illustrate two alternative structures to ensure that the lateral end 38 does not contact or abrades the cornea. Specifically, in FIG. 4(b) the lateral end 38 can have a chamfered edge 56 formed on the posterior surface thereon. The combination of a slight bend in the elongated member 32 together with the chamfered edge, eliminating any protrusion on the posterior surface, further discourages or prevents cornea or conjunctival touching. FIG. 4(c) shows that the elongated opening 54 can be eccentrically located within the elongated member 32 to cooperate with the slight angular disposition to ensure that the portion of the lateral end 38 located near the cornea does not contact or abrades the cornea. The thin retaining lip 48 is shown by dash lines on FIGS. 4(b) and 4(c).

The thin elongated lip 48 may extend beyond the body of the elongated member 32 on all but the posterior side located adjacent the cornea and conjunctiva.

FIG. 7 illustrates in a cross-sectional bottom elevational view that the elongated member 32 has a central axis 60. As is evident from the illustration in FIG. 7, lateral end 38 is slightly angularly disposed relative to the medial end 36. FIG. 7 also shows that the elongated opening 54 terminates within the elongated member 32 at a position which is between the outer edge 50 and the medial end 36. The elongated opening 54 functions as a tool receiving opening. As is apparent from the cross-sectional view of FIG. 7, the collapsible flared section 40 has curved outer walls.

FIG. 8, which is a cross-sectional bottom elevational view of another embodiment similar to FIG. 7, shows that a fluid controlled opening 62 is formed from the distal starting tip 46 through the tip insert section 44 and through the conical shaped collapsible flared section 40 into communication with the elongated opening 54. The fluid control opening 62 is used to pass or meter lacrimal fluid through the punctum plug 30. The fluid control opening 62 is selected to have a predetermined diameter to control the flow of lacrimal fluid passed therethrough. The fluid control opening can have a diameter in the range of about 0.10 mm to about 0.40 mm.

FIG. 9, which is a cross-sectional elevational bottom view of yet another embodiment of a punctum plug has a collapsible flared section 40' having sloping walls. The sloping walls in the conical flared section 40' presents a different profile than the sloping walls of the collapsible flared section 40 illustrated in FIG. 7. In FIG. 9, a fluid control opening 62, which is an alternative structure, may be formed in the punctum plug in FIG. 9. However, the fluid control opening 62 could be eliminated to form a structure which is similar to that of FIG. 7 which does not have a fluid control opening.

FIG. 10 illustrates yet another embodiment of a punctum plug wherein the collapsible flared section 64 has a non-uniform shape for enabling the collapsible flared section 64 to be collapsed relative to the central axis, such as central axis 60 illustrated in FIG. 7. In the embodiment of FIG. 10, the outer edge 66 is formed on a bias which makes the implant asymmetrical relative to the central axis of the elongated member 32. By forming an offset outer edge 66, the punctum plug can be fabricated to form a angularly shaped holding edge. FIG. 10 is illustrated to have a tip insert section 42, a shoulder 44 and distal starting tip 46 to facilitate opening of the punctum opening with less trauma and as a means for positively starting insertion of the medial end of the punctum plug 30.

FIG. 11 illustrates yet another embodiment of a punctum plug having a pair of conical shaped collapsible flared section 70 and 72 which are coaxially aligned with the central axis of the elongated member 32 and wherein the outer edges thereof are joined together to form a collapsible bellows structure. FIG. 11, in a structure similar to FIG. 10, is illustrated to have a tip insert section 42, a shoulder 44 and distal starting tip 46 to facilitate opening of the punctum opening with less trauma and as a means for positively starting insertion of the medial end of the punctum plug 30.

FIG. 12 illustrates yet another embodiment wherein the collapsible flared section 76 has two different structural features relative to the punctum plug of FIGS. 1 through 6. Specifically, the elongated member 32 is shown to be straight rather than having a slightly angular curve which is illustrated in FIGS. 1 through 6. In the embodiment of FIG. 12, the central axis 100 is straight without any angular deflection. In this structure, it may be necessary to utilize a chamfered edge as illustrated in FIG. 4(b) to avoid the lateral end 38 from contacting the cornea. The length of the elongated member can be selected to place the collapsible flared section within the vertical portion of the canaliculus wherein a clamping action of the collapsed collapsible flared section against the interior walls of the vertical portion of the canaliculus hold the punctum plug in place.

Also, the length of the elongated member can be selected to place the collapsible flared section within the ampula where the collapsible flared section reverts back to its substantially extended position.

Another structural difference in FIG. 12 resides in the fact that the collapsible flared section 76 has an outer edge 80 which is elliptically shaped.

Another embodiment wherein the collapsible flared section is elliptically shaped is shown in FIGS. 13 through 15. FIG. 13 shows, in cross-section, that the collapsible flared section 76 has curved outer walls and an outer edge which is elliptically shaped. FIG. 14 shows that the thin retaining lip 48, which may be a thin elongated retaining lip, is positioned normal to the major axis of the elliptically shaped outer edge 80. The elliptically shape of the collapsible flared section 76 provides a non-uniform collapsible flared section to enable the punctum plug to conform with the interior of the ampula which is located within the human eye.

FIG. 15 shows that the distal tip section 42 terminates in the distal starting tip 46 to facilitate a non-traumatic insertion of the punctum plug. In the alternative, the distal starting tip 46 can be tapered to eliminate the shoulder 44 as shown by 46' in FIG. 1.

FIG. 16 illustrates in a cross-sectional view the bellows structure shown in FIG. 11. The elongated opening 54 communicates with a hollowed-out central area located within each of the conical-shaped collapsible flared sections 70 and 72 and communicates with a remote tool receiving opening 82 located within the tip insert section 44.

Figure 17:
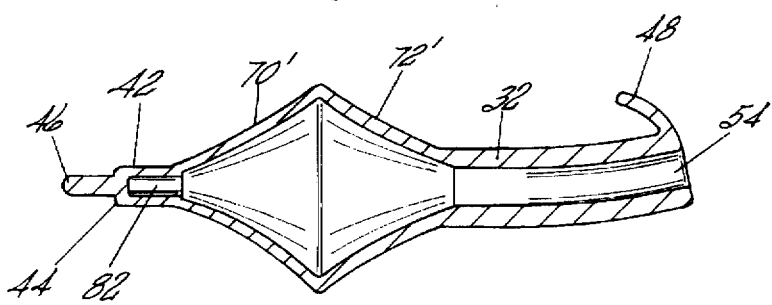
FIG. 17 is a cross-sectional bottom elevational view of yet another embodiment of a collapsible flared section in the form of a bellows defined by two conical-shaped collapsible flared sections having curved outer walls and joined at the outer edges or outer rings.

FIG. 17 shows a similar structure wherein the conical-shaped members 70' and 72' have curved outer walls.

The cross-sections of the embodiments illustrated in FIGS. 16 and 17 may be either circular or ellipitical.

Figure 18A:
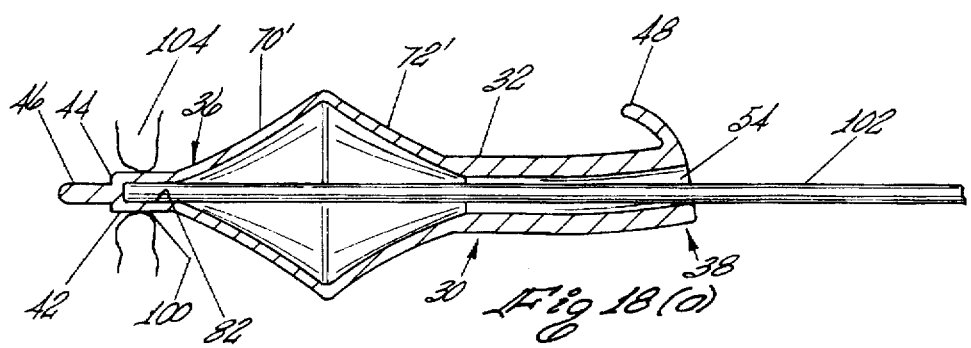
FIGS. 18(a) through 18(d) illustrate pictorially the steps of a method for inserting the punctum plug illustrated in FIG. 17 through the punctum opening and the vertical portion of the canaliculus into the ampula of an eye.

FIGS. 18(a), 18(b), 18(c) and 18(d) illustrate a method for inserting a punctum plug into the punctum opening 100 of an eye having a sphincter muscle illustrated as 104. The implant is to be transported through the punctum opening 100, through the vertical portion of a canaliculus and into the ampula to include the punctum opening 100. The implant includes elongated member 32 having a medial end 36 and a spaced, opposed lateral end 38 and a central member having a predetermined cross-sectional dimension extending from the medial end 36 to the lateral end 38. FIG. 18(a) illustrates that the distal starting tip 46 has expanded the punctum opening 100 enabling the tip insert section 42 to pass through the punctum opening 100 into the vertical portion of the canaliculus. The collapsible flared section 70' is illustrated about to be passed through the punctum opening 100. An insertion tool 102 is passed through the elongated opening 54 and into the tool receiving opening 82 to provide the insertion force at the medial end 36.

Figure 18B:
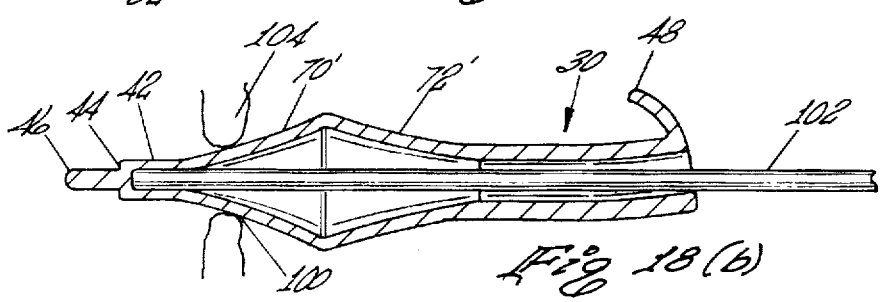

FIG. 18(b) illustrates that the collapsible flared section 70' has engaged the punctum opening 100 and the sphincter muscles 104 defining the side walls of the punctum opening 100 applies a force on the collapsible flared section 70' in a direction to collapse the same and to urge the collapsible flared section 70' from its extended position as illustrated in FIG. 18(a) to a collapsed position. As the punctum plug 30 is advanced through the punctum opening 100 and vertical portion of the canaliculus by the application of an insertion force on the insertion tool 102, the entire collapsible flared section 70' and 72', which is illustrated in FIG. 18(b) passed completely through the punctum opening 100.

Figure 18C:
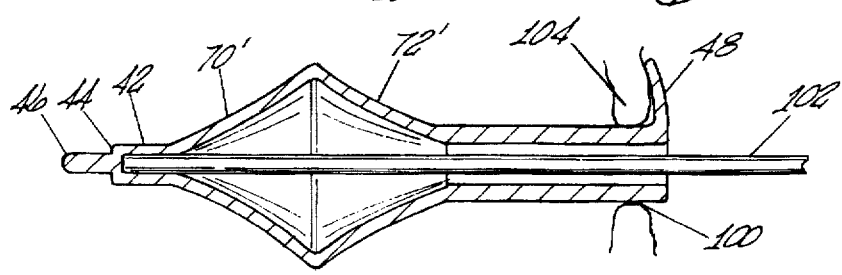

FIG. 18(c) illustrates that when the collapsible flared sections 70' and 72' are passed through the punctum opening 100 through the vertical portion of the canaliculus into the ampula, the collapsible flared sections 70' and 72' then revert back to their substantially extended positions to occlude the punctum opening and the vertical portion of the canaliculus.

Figure 18D:
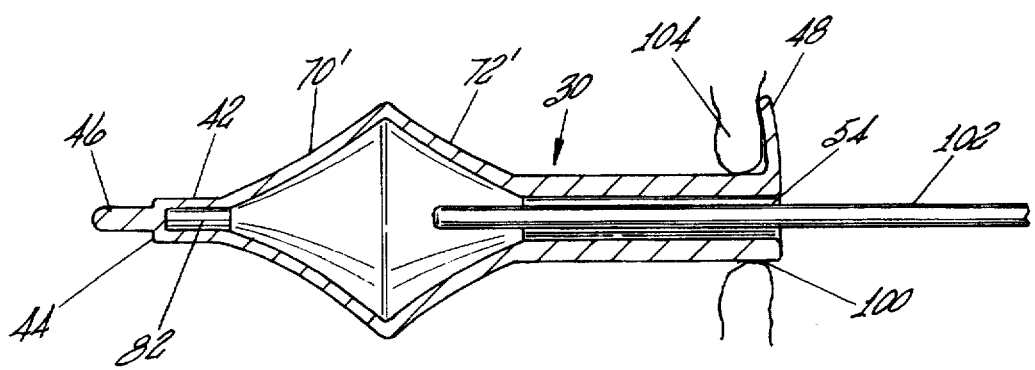

FIG. 18(d) illustrates the withdrawal of the insertion tool 102 from the inserted punctum plug 30. The thin retaining lip 48 is positioned to be located remotely from the cornea of the eye.

Figure 19:
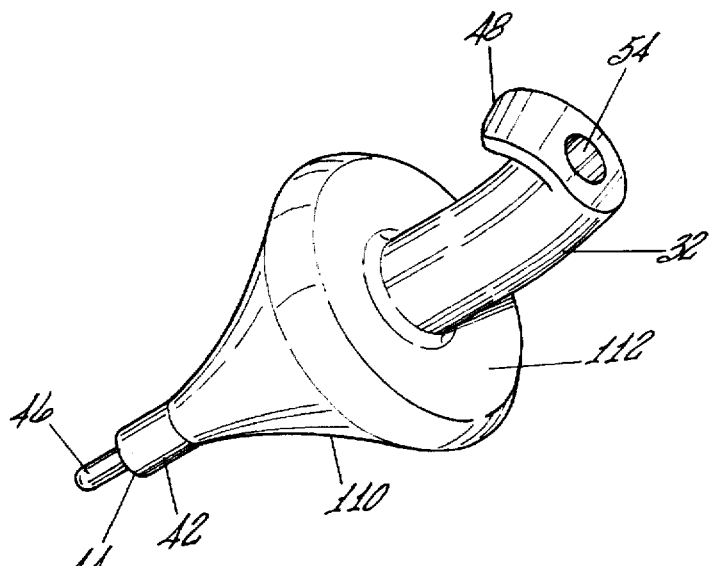
FIG. 19 is a perspective front bottom and right hand view of yet another embodiment of a punctum plug having a annular shaped balloon which defines the outer edge of a collapsible conical-shaped flared section.
Figure 20:
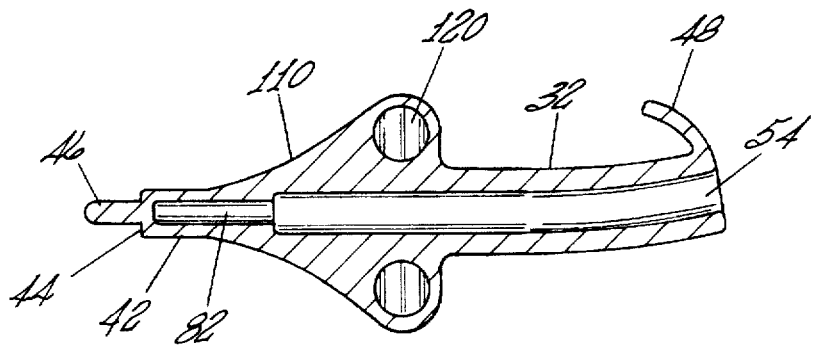
FIG. 20 is a cross sectional bottom elevational view of the punctum plug illustrated in FIG. 19 showing the position of the annular shaped balloon.

FIGS. 19 and 20 disclose yet another embodiment of an implant wherein the conical-flared section 110 is formed to have curved side walls and is formed of a resilient collapsible material. To facilitate the collapsing of the conical-shaped member which defines the collapsible flared section 110, an annular shaped balloon or opening 120 provides a collapsible space to enable the widest dimension of the implant to collapse as it is passed through the punctum opening and vertical portion of the canaliculus.

Figure 21:
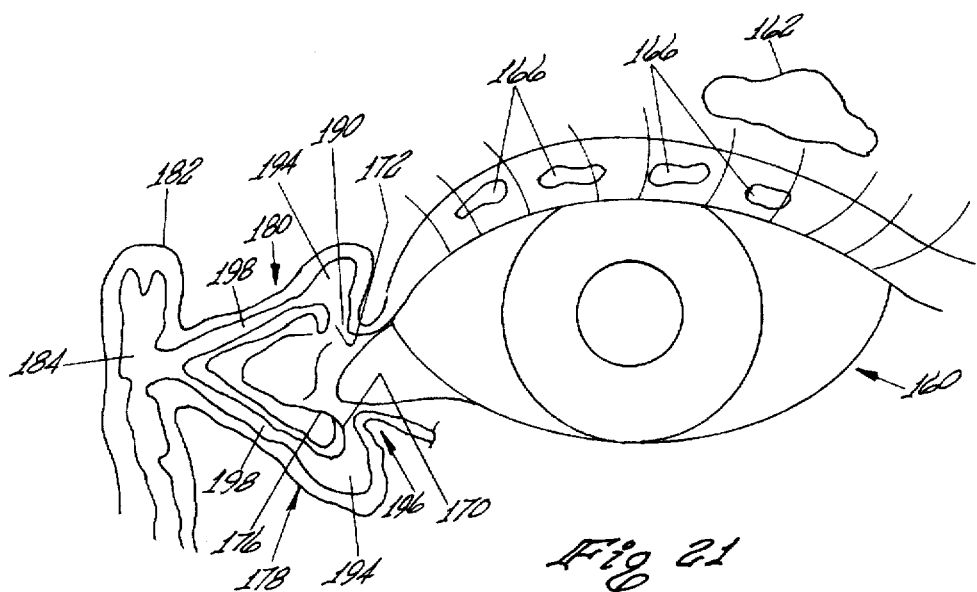
FIG. 21 is a pictorial representation of a lacrimal system of the eye having an upper and lower canaliculus, each of which have a punctum opening, vertical portion of the canaliculus, an ampula or sac and a horizontal portion of the canaliculus.

In order to better understand the teachings of the present invention, and the structure of the eye in its relationship to the present invention, the following brief description of the human eye and the associated lacrimal system illustrated in FIG. 21 and showing the paths of the tears from sources of the tears to the nasal cavity, will first be discussed.

The eye 160 includes a cornea and a pupil which is well known in the art. The source of the tears for the eye 160 is generally classified into "crying tears" and "constant tears". The "crying tears" are produced by a large lacrimal gland 162 illustrated in the upper right hand portion of the illustration of eye 160. The "constant tears" are produced by a series of small glands 166 which are located below the large gland 162 and spaced apart above the cornea of the eye 160. The "constant tears" are the tear secretions which are to be preserved in accordance with the teachings of the present invention.

In the normal eye, approximately 400 drops (9.5 milliliters) of tear secretion are produced during the day and a lesser volume of tear secretion is produced at night during sleep. Tear secretion also protects the eye from infection since the tears contain an enzyme called Lysozyme that functions as an antibiotic. With age, the eye produces less tear secretion, about sixty percent (60%) less at age 65 than at age 18. The tears flow over the eyes and drain through the small openings called the puncta, or punctal openings or punctum openings. There are two punctal openings in the eye, a lower punctum 170 and an upper punctum 172. The punctal openings 170 and 172 form openings into the corresponding a lower canaliculus 178 and an upper canaliculus 180. Each of the punctal openings 170 and 172 have the sphincter muscle, illustrated as muscle 176, formed therearound. The sphincter muscle 176 is a fairly dense relatively avascular connective ring of tissue. The lower canaliculus 178 and the upper canaliculus 180 are connected to a lacrimal sac 182. The lacrimal sac 182 is connected to a nasal lacrimal duct 184. The lacrimal duct 184, in turn, extends into the nasal cavity (not shown). The tears produced by the eye travel through the punctal openings, through their associated canaliculus.

As the tears exit the lower canaliculus 178 and the upper canaliculus 180, the tear flows merge in the lacrimal duct 184 and then travel to the nasal cavity. Lower canaliculus 178 and the upper canaliculus 180, which comprise the drainage channels of the eye travel to the nasal cavity. Lower canaliculus 178 and the upper canaliculus 180, which comprise the drainage channels of the eye are connected to an ampula or sac, shown generally as 194, which has a dimension of about 2 mm to 3 mm at its widest portion. The ampula or sac 194 narrows into the horizontal portion of the canaliculus, shown generally as 198. The medial position of the horizontal portion of the canaliculus, sometimes referred to as the horizontal canaliculus, has a diameter in the order of about 0.5 mm and an overall length of about 8 mm. In practicing the present invention, the punctum plug or implant is placed in the vertical portion 190 of the canaliculus 178 and 180.

It has developed that mechanism of lacrimal drainage results in the drainage of tear flow from the eye. One article which describes this phenomenon is entitled "BLINKING AND THE MECHANICS OF THE LACRIMAL DRAINAGE SYSTEM" by Marshall G. Doane, Ph.D., which appeared in OPHTHALMOLOGY, Volume 88, No. 8, August 1981, pages 844 through 851 inclusive (the "Doane Article"). The Doane Article describes that during each blink cycle, the upper lid sweeps down over the eye. As the lid descends, the pappillae containing the punctal opening elevate from the medial lid margin. As the lid continues to descend, the puncta are occluded by the contact of the lid margins. Further lid closure squeezes the canaliculi and sac forcing the tear or contained fluid to drain into the nasolacrimal duct. At the end of a complete lid closure, the lacrimal system is compressed and largely empty of fluid. During the opening phase, the puncta are still occluded. The walls of the passage ways or canaliculus expand by elastic force causing a partial vacuum or suction. As the lid continue to open, the puncta "pop" apart, and excess tear fluid is immediately drawn off the eye into the canaliculus.

The insertion of an implant into the ampula of the canaliculus tends to retard the squeezing action of the canaliculi during eyelid closure and to reduce the partial vacuum during eyelid opening which results in a larger quantity of tear fluid remaining on the eye. If medication is added to the eye, it remains on the eye longer thereby effecting the eye treatment by the medication which, otherwise, would be removed by the blinking and the mechanics of the lacrimal drainage system.

In utilizing the punctum plug or implant for practicing the teaching of the invention, the eye surgeon can utilize any one of a number of methods for determining if an external condition due to a deficiency of tears exists. In the preferred embodiment of the present invention, the canaliculus can be temporarily occluded by placing a temporary implant (which may be a temporary punctum plug or canalicular implant) to provide a temporary blockage of the punctum opening or canaliculus as the case may be. By utilizing a temporary implant for providing temporary blockage, the eye surgeon can observe the response of the patient to the temporary blockade. If an improvement in the eye condition of the patient is noted, a permanent punctum plug or implant can be implanted within the punctum opening and vertical portion of the canaliculus or ampula of the patient.

It is envisioned that the temporary implant used in practicing the invention can be in the form of one of the embodiments described hereinbefore with respect to FIGS. 1 through 20 of the present invention. If a punctum plug or implant is to function as a temporary implant to provide temporary blockage of the punctum opening or vertical portion of the canaliculus, the temporary implant can be fabricated from a medically acceptable, dissolvable biodegradable material such as collagen, catgut, biodegradable suturing material, polyglycolic acid or the like. The temporary punctum plug or implant can be inserted into the punctum opening and vertical portion of the canaliculus and/or ampula utilizing the procedures set forth hereinbelow in FIGS. 22(a) through 22(c).

If the eye surgeon determines that a permanent occlusion of the punctum opening and vertical portion of the canaliculus is desirable, a permanent punctum plug or implant can be utilized as a means for providing a permanent occlusion of the punctum opening and the vertical portion of the canaliculus. In such event, the permanent punctum plug or implant can be fabricated from a non-biodegradable material or material and one which is not absorbable by or dissolved in the human body. Examples of such materials are medical grade rubber, silicone, polyethylene, polypropylene, polytetrafluoroethylene (e.g. Teflon) are some of the materials. The diameter of the elongated member of the punctum plug would be in the order of about 0.2 mm to about 1.2 mm and the overall length could be in the order of about 2.5 mm to about 8 mm. The preferred diameter for elongated member of the punctum plug is in the order of about 0.5 mm to about 1.0 mm.

Figure 22A:
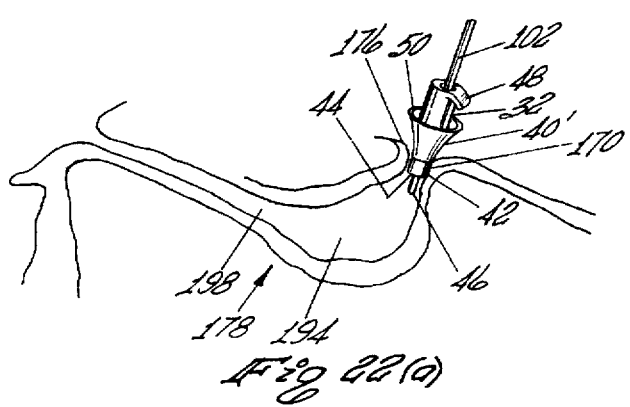
Figure 22B:
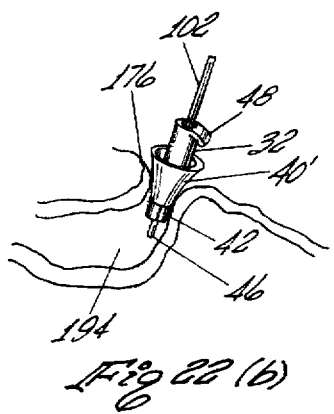
Figure 22C:
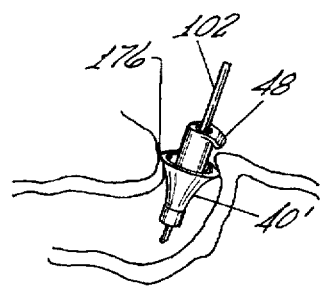
Figure 23:
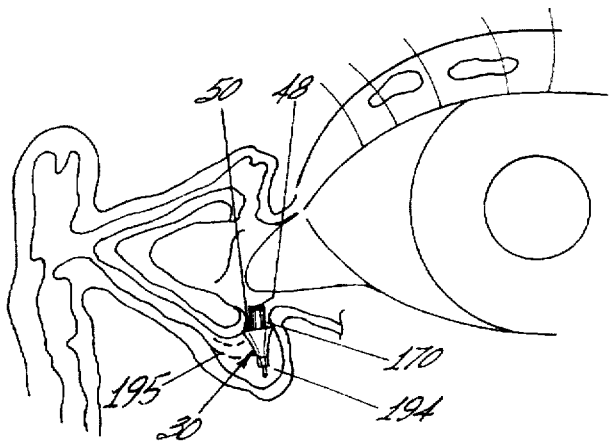
FIG. 23 is an pictorial representation showing that the collapsible flared section of the punctum plug reverts back to its substantially extended position when the same is positioned within the ampula and which occludes the punctum opening and vertical portion of the canaliculus.

Referring now to the pictorial representations of FIGS. 22(a) through 22(c). FIGS. 22(a) through 22(c) illustrate the method for inserting the punctum plug into the punctum opening and vertical portion of the canaliculus of the eye. In FIGS. 22(a) through 22(c), the pictorial representations are shown based upon the punctum plug 30 being inserted into the punctum opening, and into the vertical portion of the lower canaliculus 78. If desired, as shown in FIGS. 22(c) and 23, the length of the punctum plug can be selected to place the collapsible flared section into the ampula 194. Of course, the punctum plug 30 could be inserted into the upper canaliculus 180 in a similar manner as described below. As illustrated in FIG. 22(a), an insertion tool 102 is inserted into the elongated opening 54 of the central member 32 and extends into the collapsible flared section 40' of the punctum plug and cooperates with the central section thereof such that the distal end or tip of the insertion tool 102 is positioned below the outer edge 50 defined by the thin-walled, conical-shaped member of the collapsible flared section 40'. The punctum plug 30 is positioned with the distal starting tip 46 of the tip insert section 44 located on the medial end 36 penetrating the punctal opening 170 such that the medial tip 36 will gently expand the sphincter muscle 176 defining the punctal opening 170. The collapsible flared section 40' is then passed through the punctal opening 170 until the punctal opening engages the exterior surface of the collapsible flared section 40'.

FIG. 22(b) illustrates that the sphincter muscle 176 slightly engages the collapsible flared section 40' as an insertion force is applied to the punctum plug 30 by the insertion tool 102. A radial force is applied around the surface of the collapsible flared section 40' as the punctum plug 30 slideably moves past the sphincter muscle 176. The sphincter muscle 176 applies a radial force to the collapsible flared section 40' in a direction so as to cause the collapsible flared section to be urged into its collapsed position. A clamping force is developed between the outer walls of the collapsed conical-shaped member defining the collapsible flared section 40' and the inner walls of the vertical section of the canaliculus holding the implant in place.

If the punctum plug is selected to have sufficient length to be inserted past the vertical portion of the canaliculus, then FIG. 22(c) illustrates that the insertion tool 102 continually applies an insertion force transporting the punctum plug 30 through the vertical portion of the canaliculus 190 and into the ampula or sac 194. Due to the increased diameter of the ampula or sac, the radial force is no longer applied against the collapsible flared section 40' and the collapsible flared section 40' that reverts back to its substantially extended position to occlude the punctum opening and the vertical portion of at least one canaliculi.

This is illustrated in great detail in FIG. 23 wherein the angular curve between the medial end and lateral end is evident. The size, uniformity or non-uniformity of the punctum plug can be selected to provide the best conformity between the collapsible flared section and the size and shape of the interior of the ampula 190. For example, an elliptically shaped collapsible flared section as illustrated in FIGS. 12 through 15 may be the best punctum plug to provide occlusion of the punctum opening and vertical portion of the canaliculus than other embodiments illustrated herein. In such event, it would be preferable to use such a punctum plug having a non-uniform shape in lieu of a collapsible flared section having a uniform shaped and/or generally circular cross-section. If a punctum plug having a length in the order of 8 mm is used, dashed lines 195 illustrate the orientation of the medial end of the punctum plug.

In the alternative, a punctum plug having a structure illustrated in FIG. 10 with a bias outer edge 66 may hold better in the ampula, depending on the physical size and shape thereof. It is envisioned that an image could be made of the punctum opening, vertical portion of the canaliculus and ampula size and shape and that the physical size, shape including the length of the elongated member 32 be selected to best fit the geometry of the eye.

Figure 24:
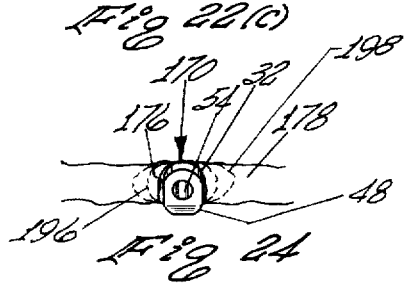
FIG. 24 is an enlarged pictorial representation of the thin elongated retaining lip in contact with the sphincter muscle defining the punctum opening with the retaining lip being positioned away from the cornea.

FIG. 24 illustrates pictorially the location of the thin retaining lip 48 over the edge of the punctum opening 170 which is defined by the sphincter muscle 176 in the lower eyelid 178. Due to the angular curvature of the lateral end relative to the medial end, the thin retaining lip 48 is urged away from the cornea and engages the sphincter muscle 176. The punctum plug 30 is held in place by the action of the collapsible flared section 40' and the thin retaining lip 48. If the collapsible flared section is located in the ampula 194 as shown in FIG. 23, then the outer edge 50 cooperates with the ampula to hold the medial end of the punctum plug in place and the thin retaining lip 48 holds the lateral end of the punctum plug in place to prevent migration thereof. Also, FIG. 24 has a dashed outline 196 illustrating diagrammatically a collapsible flared section having a generally circular cross-section and a dashed outline 198 illustrating diagrammatically a collapsible flared section having a generally elliptical cross-section.

If the collapsible flared section is located in the punctum opening and the vertical portion of the canaliculus, a clamping force is developed to hold the medial end of the punctum plug in place and the thin retaining lip 48 holds the lateral end of the punctum plug in place to prevent migration thereof.

By utilizing the teachings of the present invention, a method for treating external eye conditions due to a deficiency of tears is disclosed. The method includes the steps of testing the eye to determine if a tear deficiency exists; and, if a tear deficiency is determined, placing a punctum plug having an elongated member, a first end and a second end wherein the first end has a thin retaining lip and a second end having a collapsible flared section, within the punctum opening and vertical portion of at least one of the canaliculi.

The present invention also teaches a method for surgically inserting an implant through a punctum opening into the vertical portion of at least one of the canaliculi having interior side walls of an eye for treating external eye condition due to a deficiency of tears. The method comprises the steps of inserting a punctum plug having an elongated central member and a pair of ends wherein one end of said pair of ends has a collapsible flared section terminating in a starting tip and the other of said pair of ends has a thin retaining lip and wherein the starting tip and collapsible flared section pass through the punctum opening and into the vertical portion of at least one of the canaliculi interior of the eye causing the collapsed flared section to be collapsed as it passes through the punctum opening and vertical portion of the canaliculi and to return to its extended position within the ampula located adjacent to the vertical portion of said at least one canaliculi to occlude the punctum opening and the vertical portion of the canaliculus.

The step of urging in the above described method can include using a tool which is inserted into the collapsible flared section to apply force to urge the punctum plug through the punctum opening, through the vertical section of at least one of the canaliculi and into the ampula.

The punctum plug or implant of the present invention utilizes the collapsible flared section as a means for occluding the punctum opening and the vertical portion of a canaliculi if a short elongated member is used. In such event, the collapsible flared section will remain in a collapsed position and a clamping force is developed between the collapsible flared section and the interior walls of the vertical portion of the canaliculus to hold the punctum plug in place.

If the length of the punctum plug is selected to extend the collapsible flared section into the ampula, the force which collapses the collapsible flared section is no longer present and the collapsible flared section then reverts back into its substantially extended position.

The punctum plug of the present invention is preferably used as a permanent implant for practicing the invention. In the method disclosed and taught herein, the temporary implant could be an implant well known in the art, could be a means for occluding the punctum opening and vertical portion of the canaliculus, could be a temporary implant as disclosed in the prior art section above or any other means known in the art for temporarily occluding the eye to determine if an improvement in eye condition is noted.

However, the temporary implant could, likewise, be a punctum plug or implant having a structure disclosed herein wherein the implant is formed of an absorbable or dissolvable (in the body) biodegradable material. The permanent punctum plug or implant can be identical in shape, size and dimension but be formed of a non-biodegradable, nonabsorbable or non-dissolvable (in the body) material. The advantage of utilizing a temporary implant and a permanent implant which has a structure as disclosed herein is that the collapsible flared section of the canalicular implant performs the function of occluding the punctum opening and/or the vertical section of the canaliculus. If the punctum plug does not extend all the way into the ampula and remains within the punctum opening and the vertical portion of the canaliculus, the collapsible flared section develops a clamping pressure between the collapsible flared section and the interior walls of the punctum opening or the vertical portion of the canaliculus while providing the desired blockage to the eye.

If it is desirable to have a small passageway available to enable a limited flow of tears to pass through the occlusion, it is envisioned that the punctum plug or implant could have an aperture extending axially through the center thereof. For example, the punctum plug could have a lacrimal fluid control opening such as shown by opening 62 in FIGS. 8 and 9, to provide a passageway of a predetermined diameter to control tear secretion flow or, the alternative, a slot could be formed around the periphery thereof to facilitate a partial tear flow.

It is also envisioned that the punctum plug or implant of the present invention could include material which is responsive to actinic radiation, such as for example X-rays, so that the eye surgeon can perform tests to determine if the punctum plug or implant is properly located within the punctum opening and vertical section of the canaliculus. One such material that can be utilized is barium, in appropriate concentrations known to persons skilled in the art, so as to be responsive to actinic radiation, such as X-rays. The use of such materials responsive to actinic radiation is of such a low enough level that it does not cause any adverse effects to the patient into which a punctum plug or implant containing the same is implanted.

Typical dimensions for the punctum plug may include the elongated member having a diameter of about 0.5 mm to about 1.2 mm. The diameter of the outer ring defining the outer edge of the collapsible flared section may be in the order of about 1.5 mm to about 2.5 mm. The overall length of the implant could be about 2.5 mm to about 8 mm.

The diameter of the distal starting tip can be about 0.2 mm to about 0.4 mm with about 0.3 mm being preferred.

What is claimed is:

1. An implant comprising an elongated member having a pair of ends wherein one of said pair of ends includes a collapsible flared section having an outer surface and the other of said pair of ends includes a thin elongated lip, said thin elongated lip being located on said elongated member to position the thin elongated tip in a generally anterior direction upon insertion in to a punctum opening, said elongated member and said collapsible flared section being formed of a dimension to pass through a punctum opening of an eye.

2. The implant of claim 1 wherein the elongated member curves slightly in a direction towards said other of said pair of ends.

3. The implant of claim 1 wherein said elongated member has a central axis and wherein said collapsible flared section is collapsible relative to said central axis in response to the application of a force on the collapsible flared section in a direction to collapse the same and urge the collapsible flared section into a collapsed position.

4. The implant of claim 3 wherein said collapsible flared section has a substantially uniform shape for enabling said collapsible flared section to be uniformly collapsed relative to said central axis.

5. The implant of claim 4 wherein said collapsible flared section is in the form of a bellows.

6. The implant of claim 4 wherein said collapsible flared section has an outer edge formed on a bias relative to the central axis.

7. The implant of claim 4 wherein said collapsible flared section includes a collapsible annular balloon.

8. The implant of claim 1 wherein said collapsible flared section has a substantially uniform shape for enabling said collapsible flared section to be uniformly collapsed relative to said central axis.

9. The implant of claim 1 wherein said collapsible flared section has a hollowed out central area defining a thin-walled, conical shaped member.

10. The implant of claim 1 wherein said collapsible flared section has an outer edge which is located between said pair of ends.

11. The implant of claim 10 wherein said collapsible flared section has a substantially circular shaped outer edge which is located adjacent said one of said pair of ends.

12. The implant of claim 1 wherein said elongated member has a central axis and wherein said collapsible flared section has a non-uniform shape for enabling said collapsed flared section to be collapsed relative to said central axis.

13. The implant of claim 1 having a fluid control opening extending therethrough to pass lacrimal fluid.

14. The implant of claim 13 wherein said fluid control opening is selected to have a predetermined diameter to control the flow of lacrimal fluid passed therethrough.

15. The implant of claim 14 wherein said fluid control opening has a diameter in the range of about 0.10 mm to about 0.40 mm.

16. A punctum plug comprising
an elongated central member having a central axis and a pair of ends wherein one of said pair of ends includes means defining a collapsible flared section which is capable of being collapsed relative to said central axis in response to the application of force on the collapsible flared section in a direction to collapse the same and urge the collapsible flared section into a collapsed position and the other of said pair of ends includes a thin elongated lip, said thin elongated lip being located on said elongated member to position the thin elongated tip in a generally anterior direction upon insertion in to a punctum opening, said elongated central member and said collapsible flared section being formed of a dimension to pass through a punctum of an eye.

17. An implant comprising
an elongated central member having a central axis, a first end and a second end wherein said first end curves angularly relative to said second end and wherein said first end includes a thin elongated lip, said thin elongated lip being located on said elongated member to position the thin elongated tip in a generally anterior direction upon insertion in to a punctum opening, said second end has a collapsible flared section having a preselected shape and wherein said collapsible flared section includes means for enabling said collapsible flared section to be collapsed relative to said central axis in response to the application of force on the collapsible flared section in a direction to collapse the same and urge the collapsible flared section into a collapsed position, said elongated central member and said collapsible flared section being formed of a dimension to pass through a punctum of an eye.

18. The implant of claim 17 wherein said collapsible flared section has a substantially circular cross-section.

19. The implant of claim 18 wherein the second end terminates in a tip insert section having predetermined cross-sectional dimension and wherein the tip insert section has a distal starting tip which is smaller in cross-sectional dimension than said tip insert section.

20. The implant of claim 19 wherein said distal starting tip has a sloped surface.

21. The implant of claim 19 wherein said collapsible flared section has an initial cross-sectional dimension at said second end which is substantially equal to said predetermined cross-sectional dimension and which increases in cross-sectional dimension as said collapsible flared section extends towards said first end.

22. The implant of claim 21 wherein said collapsible flared section terminates in an outer edge.

23. The implant of claim 22 wherein said collapsible flared section and outer edge are elliptically shaped and said collapsible flared section is responsive to a force applied in direction to collapse the same to urge the collapsible flared section into a collapsed position.

24. The implant of claim 17 wherein said collapsible flared section has an angular shaped balloon defining an outer edge of the collapsible flared section.

25. The implant of claim 17 wherein said collapsible flared section comprises a pair of conical-shaped collapsible flared sections having their outer edges joined together.

26. The implant of claim 17 wherein said elongated central member has a tool receiving opening.

27. The implant of claim 26 wherein said tool receiving opening extends from a location adjacent said second end, through the elongated central member and through said first end.

28. A punctum plug comprising
an elongated member having a central axis, first end, a second end and a central section extending between said first end and said second end;
said elongated member having a slight angular curve which deflects said first end in a selected angle from said second end, said first end having a thin elongated lip, said thin elongated lip being located on said elongated member to position the thin elongated tip in a generally anterior direction upon insertion in to a punctum opening; and
said second end having a collapsible flared section which increases in cross-section as the collapsible flared section approaches the first end, said collapsible flared section having an extended position and a collapsed position, said collapsible flared section when an extended position being responsive to the application of a force in a direction to collapse the same by being urged into its collapsed position.

29. The implant of claim 28 wherein said collapsible flared section has a hollowed-out central area defining a thin-walled, conical-shaped member.

30. The implant of claim 29 wherein said thin-walled, conical-shaped member terminates in an outer edge.

31. The implant of claim 30 wherein said outer edge is in the form of an outer ring.

32. The implant of claim 31 wherein the diameter of the annular-shaped outer ring is in the order of about 1.5 mm to about 2.0 mm.

33. The implant of claim 29 wherein the overall length of the implant is about 2.5 mm to about 8 mm.

34. The implant of claim 29 wherein the second end terminates in a tip insertion section having a distal starting tip.

35. The implant of claim 34 wherein the diameter of the distal starting tip is about 0.2 mm to about 0.4 mm.

36. The implant of claim 35 wherein the diameter of the distal starting tip is about 0.3 mm.

37. The implant of claim 28 wherein the cross-section of the central section is generally circular in shape.

38. The implant of claim 37 wherein the diameter of the generally circular shaped central section is between about 0.7 mm to about 1.0 mm.

39. The implant of claim 28 wherein the implant is formed of a biodegradable material.

40. The implant of claim 39 wherein the biodegradable material is a collagen material.

41. The implant of claim 28 wherein the implant is formed of a non-biodegradable material.

42. The implant of claim 41 wherein the non-biodegradable material is a silicone material.

43. An implant adapted to be inserted into the punctum opening of an eye and be transported through the vertical portion of the canaliculus into the ampula to occlude the punctum opening and vertical portion, said implant comprising an elongated member having a medial end and a spaced, opposed lateral end and a central member having a predetermined cross-sectional dimension extending from said medial end to said lateral end;

said medial end having a collapsible flared section which increases in cross-section as the collapsible flared section approaches the lateral end and which terminates in an outer edge having a dimension which is greater than the predetermined cross-sectional dimension of the central member, said collapsible flared section having an extended position and a collapsed position wherein the dimension of the collapsed position is approximately equal to a geometrical dimension of the punctum opening of an eye adapted to pass the same, and wherein the application of a radial force in a direction to collapse the collapsible flared section urges the same from its extended position into its collapsed position, and said lateral end including a thin elongated lip, said thin elongated lip being located on said elongated member to position the thin elongated tip in a generally anterior direction upon insertion in to a punctum opening.

44. The implant of claim 43 wherein the elongated member has a slightly angular curve in a selected direction causing the lateral end to be slightly deflected relative to the medial end for urging the lip into holding engagement with the punctum opening.

* * * * *